(12) United States Patent
Zelkovich et al.

(10) Patent No.: US 8,496,862 B2
(45) Date of Patent: Jul. 30, 2013

(54) COLLET MECHANISM AND METHOD OF MOLDING CANNULA TO A SYRINGE BARREL

(75) Inventors: Matthew J. Zelkovich, Scottsdale, AZ (US); John Baker, Scottsdale, AZ (US); Todd E. Kuhn, Scottsdale, AZ (US); Paul Roussel, Scottsdale, AZ (US); Jon Lundquist, Chandler, AZ (US)

(73) Assignee: West Pharmaceutical Services, Inc., Exton, PA (US)

( * ) Notice: Subject to any disclaimer, the term of this patent is extended or adjusted under 35 U.S.C. 154(b) by 1008 days.

(21) Appl. No.: 12/680,609

(22) PCT Filed: Jan. 15, 2009

(86) PCT No.: PCT/US2009/031112
§ 371 (c)(1),
(2), (4) Date: Mar. 29, 2010

(87) PCT Pub. No.: WO2009/091895
PCT Pub. Date: Jul. 23, 2009

(65) Prior Publication Data
US 2010/0270702 A1    Oct. 28, 2010

Related U.S. Application Data

(60) Provisional application No. 61/021,186, filed on Jan. 15, 2008.

(51) Int. Cl.
*B29C 45/14* (2006.01)
*B29B 13/00* (2006.01)
*B29B 7/00* (2006.01)
*A23G 1/22* (2006.01)
*A61M 5/315* (2006.01)
*A61M 5/00* (2006.01)

(52) U.S. Cl.
USPC ........ 264/278; 264/259; 264/271.1; 264/275; 264/279; 264/328.1

(58) Field of Classification Search
USPC ........... 264/259, 271.1, 275, 278, 279, 328.1; 604/181, 187, 207, 218, 221; 425/110, 121, 425/190, 192 R, 468
See application file for complete search history.

(56) References Cited

U.S. PATENT DOCUMENTS

| | | |
|---|---|---|
| 2,998,050 A | 8/1961 | Hamilton et al. |
| 3,093,134 A | 6/1963 | Roehr |

(Continued)

FOREIGN PATENT DOCUMENTS

| | | |
|---|---|---|
| CH | 657990 A5 | 10/1986 |
| EP | 0350792 | 1/1990 |

(Continued)

OTHER PUBLICATIONS

Office Action issued Sep. 21, 2009 in U.S. Appl. No. 29/334,048.

(Continued)

*Primary Examiner* — Christina Johnson
*Assistant Examiner* — Atul P. Khare
(74) *Attorney, Agent, or Firm* — Panitch Schwarze Belisario & Nadel LLP (57) ABSTRACT

A collet mechanism that holds a cannula during molding of a syringe includes first and second arms that form an internal cavity. Each arm has a proximal end and a distal end. The first and second arms are in a closed position when the distal ends are moved toward the internal cavity and are in an open position when the distal ends are positioned away from the internal cavity. First and second cannula guides respectively are mounted proximate the distal ends of the first and second arms and extend into the internal cavity. The first and second cannula guides clamp a portion of the cannula to hold the cannula when the first and second arms are in the closed position.

8 Claims, 10 Drawing Sheets

U.S. PATENT DOCUMENTS

| | | | |
|---|---|---|---|
| 3,118,448 A | | 1/1964 | Gottschalk |
| 3,135,993 A | * | 6/1964 | Ryan .......................... 264/275 |
| 3,330,004 A | * | 7/1967 | Cloyd et al. ................. 72/386 |
| 3,359,619 A | | 12/1967 | Walkden |
| 3,470,604 A | | 10/1969 | Zenick |
| 3,648,684 A | | 3/1972 | Barnwell et al. |
| 3,756,235 A | | 9/1973 | Burke et al. |
| 3,782,383 A | | 1/1974 | Thompson et al. |
| 3,865,236 A | | 2/1975 | Rycroft |
| D238,617 S | | 1/1976 | Evanston |
| 3,943,225 A | | 3/1976 | Koehn |
| 4,003,262 A | | 1/1977 | Gerarde et al. |
| 4,070,756 A | | 1/1978 | Shields |
| 4,263,922 A | | 4/1981 | White |
| D262,739 S | | 1/1982 | Nitshke |
| 4,367,738 A | | 1/1983 | Legendre et al. |
| 4,367,749 A | | 1/1983 | Dudley et al. |
| 4,391,273 A | | 7/1983 | Chiquiar-Arias |
| 4,392,497 A | | 7/1983 | Ghaussy |
| 4,441,951 A | | 4/1984 | Christinger |
| 4,513,754 A | * | 4/1985 | Lee .............................. 600/566 |
| 4,581,024 A | | 4/1986 | Swenson |
| 4,585,444 A | | 4/1986 | Harris |
| 4,589,871 A | | 5/1986 | Imbert |
| 4,617,012 A | | 10/1986 | Vaillancourt |
| 4,655,764 A | | 4/1987 | Sato |
| 4,675,007 A | | 6/1987 | Terry |
| 4,742,910 A | | 5/1988 | Staebler |
| 4,795,445 A | | 1/1989 | Jensen |
| 4,838,877 A | | 6/1989 | Massau |
| 4,840,185 A | | 6/1989 | Hernandez |
| 4,886,072 A | | 12/1989 | Percarpio et al. |
| 4,915,225 A | | 4/1990 | Tabor, Jr. et al. |
| 4,922,602 A | | 5/1990 | Mehl |
| 4,936,833 A | | 6/1990 | Sams |
| 4,972,843 A | | 11/1990 | Broden |
| 4,976,925 A | | 12/1990 | Porcher et al. |
| 5,026,355 A | | 6/1991 | Sweeney et al. |
| D321,759 S | | 11/1991 | Buswell et al. |
| 5,087,249 A | | 2/1992 | Deal |
| 5,125,058 A | | 6/1992 | Tenerz et al. |
| 5,183,469 A | | 2/1993 | Capaccio |
| 5,312,351 A | | 5/1994 | Gerrone |
| 5,364,369 A | | 11/1994 | Reynolds et al. |
| 5,489,272 A | | 2/1996 | Wirtz |
| 5,510,065 A | | 4/1996 | McFarlane |
| 5,529,189 A | | 6/1996 | Feldschuh |
| D377,687 S | | 1/1997 | Udovch |
| 5,607,399 A | | 3/1997 | Grimard et al. |
| 5,616,136 A | | 4/1997 | Shillington et al. |
| 5,667,495 A | | 9/1997 | Bitdinger et al. |
| D387,425 S | | 12/1997 | Niedospial et al. |
| 5,693,028 A | | 12/1997 | Shillington |
| 5,700,247 A | | 12/1997 | Grimard et al. |
| 5,803,918 A | | 9/1998 | Vetter et al. |
| D403,761 S | | 1/1999 | Adams |
| 5,980,495 A | | 11/1999 | Heinz et al. |
| D417,730 S | | 12/1999 | Brassil et al. |
| 5,997,511 A | | 12/1999 | Curie et al. |
| D419,671 S | | 1/2000 | Jansen |
| 6,223,408 B1 | | 5/2001 | Vetter et al. |
| 6,331,174 B1 | | 12/2001 | Reinhard et al. |
| 6,361,525 B2 | | 3/2002 | Capes et al. |
| 6,494,892 B1 | | 12/2002 | Ireland et al. |
| 6,537,259 B1 | | 3/2003 | Niermann |
| 6,558,353 B2 | | 5/2003 | Zohmann |
| D476,417 S | | 6/2003 | Swenson et al. |
| 6,589,261 B1 | | 7/2003 | Abulhaj et al. |
| 6,616,639 B2 | | 9/2003 | Gagnieux et al. |
| 6,629,962 B2 | | 10/2003 | Correa et al. |
| 6,709,428 B2 | | 3/2004 | Sagstetter |
| 6,723,111 B2 | | 4/2004 | Abulhaj et al. |
| D490,517 S | | 5/2004 | Harmon |
| D492,404 S | | 6/2004 | Prais et al. |
| RE38,964 E | | 1/2006 | Shillington |
| 7,024,749 B2 | | 4/2006 | Sagstetter |
| D558,340 S | | 12/2007 | Hochman et al. |
| 7,418,880 B1 | | 9/2008 | Smith |
| D578,210 S | | 10/2008 | Muta et al. |
| 7,455,661 B2 | | 11/2008 | Barrelle et al. |
| D588,693 S | | 3/2009 | Strong et al. |
| 7,544,189 B2 | | 6/2009 | Griffiths |
| 7,582,073 B2 | | 9/2009 | Barrelle et al. |
| D609,333 S | | 2/2010 | Holmes |
| D617,453 S | | 6/2010 | Shaw |
| 7,874,827 B2 | * | 1/2011 | Togashi et al. ................ 425/190 |
| D635,249 S | | 3/2011 | Becker |
| D638,122 S | | 5/2011 | Kosinski et al. |
| 8,002,754 B2 | | 8/2011 | Kawamura et al. |
| 8,021,511 B2 | | 9/2011 | Erskine |
| D650,903 S | | 12/2011 | Kosinski et al. |
| 8,105,294 B2 | * | 1/2012 | Araki et al. ................... 604/207 |
| 8,313,954 B2 | | 11/2012 | Leach et al. |
| 2001/0049496 A1 | | 12/2001 | Kirchhofer et al. |
| 2002/0007147 A1 | | 1/2002 | Capes et al. |
| 2002/0026146 A1 | | 2/2002 | Jansen et al. |
| 2002/0133184 A1 | | 9/2002 | LoRusso |
| 2003/0069544 A1 | | 4/2003 | Lee |
| 2003/0088215 A1 | | 5/2003 | Ferguson et al. |
| 2003/0088234 A1 | | 5/2003 | Sagstetter |
| 2004/0002713 A1 | | 1/2004 | Olson et al. |
| 2004/0127857 A1 | | 7/2004 | Shemesh et al. |
| 2006/0079848 A1 | | 4/2006 | Pelkey et al. |
| 2006/0200085 A1 | | 9/2006 | Watts et al. |
| 2006/0200095 A1 | | 9/2006 | Steube |
| 2007/0167912 A1 | | 7/2007 | Causey et al. |
| 2007/0185460 A1 | | 8/2007 | Vedrine et al. |
| 2007/0239117 A1 | | 10/2007 | Chelak et al. |
| 2007/0265582 A1 | | 11/2007 | Kaplan et al. |
| 2007/0286881 A1 | | 12/2007 | Burkinshsw |
| 2008/0183137 A1 | | 7/2008 | Barrelle et al. |
| 2008/0269688 A1 | | 10/2008 | Colucci et al. |
| 2009/0157044 A1 | | 6/2009 | Liyanagama et al. |
| 2010/0145284 A1 | * | 6/2010 | Togashi ........................ 604/218 |
| 2010/0152678 A1 | | 6/2010 | Jakob |
| 2012/0010573 A1 | | 1/2012 | Lundquist |
| 2012/0022457 A1 | | 1/2012 | Silver |
| 2012/0078179 A1 | | 3/2012 | Finke |

FOREIGN PATENT DOCUMENTS

| | | |
|---|---|---|
| FR | 1004756 A | 4/1952 |
| GB | 614003 A | 12/1948 |
| GB | 1207229 A | 9/1970 |
| JP | 4303730 | 10/1992 |
| WO | 2012043544 A1 | 4/2012 |

OTHER PUBLICATIONS

Office Action issued Mar. 18, 2010 in U.S. Appl. No. 29/334,048.

U.S. Appl. No. 29/402,109 by Lundquist, filed Sep. 21, 2011.

International Preliminary Report on Patentability Issued Jul. 20, 2010 in Int'l Application No. PCT/US2009/031112; Written Opinion.

International Search Report Issued Oct. 22, 2009 in Int'l Appln. No. PCT/US2009/031112; Written Opinion.

Office Action issued Jul. 31, 2012 in JP Application No. 2010-543235.

Extended search report issued Jun. 12, 2012 in EP Application No. 12166374.4.

Extended search report issued Sep. 7, 2011 in EP Application No. 09702776.7.

U.S. App. No. 29/427,516 by Lundquist, filed Jul. 19, 2012.

Office Action issued Nov. 26, 2012 in CN Application No. 200980101066.7.

Office Action issued Apr. 23, 2013 in U.S. Appl. No. 29/402,109.

* cited by examiner

COLLET MECHANISM AND METHOD OF MOLDING CANNULA TO A SYRINGE BARREL

CROSS-REFERENCE TO RELATED APPLICATION

This application is a Section 371 of International Application No. PCT/US09/031,112, filed Jan. 15, 2009, which was published in the English language on Jul. 23, 2009 under International Publication No. WO 2009/091895 A2, and the disclosure of which is incorporated herein by reference.

BACKGROUND OF THE INVENTION

The present invention relates to a collet mechanism and a method of molding a cannula to a syringe barrel, specifically the collet mechanism and method of molding a fine gauge cannula to a polymeric syringe barrel to form a staked needle device.

The process of bonding a cannula to a syringe barrel is a critical step in the manufacture of syringes. The cannula must be precisely positioned and then bonded to the syringe without being damaged. The slightest bend or burr in the end of the cannula increases the perceived pain by a patient. The cannula is preferably directly inline with the center axis of the syringe. The cannula must also be sufficiently bonded to the syringe to withstand a minimum 22N pull test rating in accordance with the International Standards Organization's (ISO's) standards. For polymeric syringes, the cannula is typically interference fit into a preformed syringe barrel in a similar manner to what is done with a glass syringe. The cannula is often affixed to the syringe by an adhesive. However, it is undesirable to use an adhesive to affix a cannula to a syringe because the adhesive may contain toxic chemicals that could leach into the syringe contents, comprised of one or more drug(s)/biological compound(s), and could alter the efficacy and/or stability of the syringe contents that eventually enter the patient.

In order to avoid the use of an adhesive, the cannula (typically a 25 gauge needle or larger) is typically crimped toward its proximal end and then the syringe barrel is insert molded over the proximal end of the cannula, so that the syringe molds over the crimped proximal end to securely grip and retain the cannula to the syringe. Though crimping the proximal end may avoid the use of an adhesive, finer gauge cannulas (i.e. 27 to 33 gauge) cannot usually be crimped without potentially damaging the cannula due to their small physical dimensions. Specifically, due to the very thin wall of the tubing of such finer gauge cannulas, it is physically impossible to crimp the outside diameter of such cannulas without completely closing down the inner diameter of the cannulas. Regardless of the attachment method, it is difficult to position, hold, and/or mount a fragile, fine gauge cannula without damaging the cannula.

What is therefore needed, but not provided in the prior art, is a mechanism that holds the cannula, particularly a small diameter cannula, in place during the molding process to securely attach the cannula directly to a polymeric syringe barrel without the use of an adhesive or the need to crimp the cannula, and without damaging the cannula, specifically the sharp beveled tip of the cannula.

BRIEF SUMMARY OF THE INVENTION

Briefly stated, the present application is directed to a collet mechanism for holding a cannula during molding of a syringe. The collet mechanism includes first and second arms which form an internal cavity. Each arm has a proximal end and a distal end. The first and second arms are in a closed position when the distal ends are moved toward the internal cavity and are in an open position when the distal ends are positioned away from the internal cavity. First and second cannula guides respectively are mounted proximate the distal ends of the first and second arms and extend into the internal cavity. The first and second cannula guides clamp a portion of the cannula to hold the cannula when the first and second arms are in the closed position.

In another aspect, the present application is directed to a method of manufacturing a syringe. The method includes the steps of: placing a cannula having a beveled tip onto a recessed tip of a core member; placing a mold over the core member, the mold having a tapered receiving port at least partially surrounding at least a portion the cannula; inserting a collet mechanism having at least two cannula guides through the mold and over the beveled tip of the cannula, a distal end of the collet mechanism being guided by the tapered receiving port to move the collet mechanism into a closed position wherein the cannula guides clamp a portion of the cannula to hold the cannula generally in alignment with a longitudinal axis of the collet mechanism and with a longitudinal axis of the core member; injecting polymeric material into the mold; allowing the polymeric material to cool until substantially solidified over at least a proximal end of the cannula; removing the collet mechanism from the mold such that the cannula guides release the cannula; removing the mold; and removing the syringe and attached cannula from the core member.

In a further aspect, the present application is directed to a cannula having an outside diameter in the range of 0.0080 to 0.0165 inches for attachment to a tip of a polymeric syringe barrel that is molded over the cannula. At least a portion of a proximal end of the cannula has a plurality of notches formed on an outer surface.

BRIEF DESCRIPTION OF THE SEVERAL VIEWS OF THE DRAWINGS

The following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the collet mechanism and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings, wherein like numerals indicate like elements throughout, there is shown in FIGS. 3-7 and 11-13 a first preferred embodiment of a collet mechanism 10. The collet mechanism 10 is used to position and hold a cannula 12 in place during insert or another type of molding of a staked needle, generally 14, without damaging the cannula 12.

Referring to FIGS. 1A-2C, the staked needle 14 is comprised of a polymeric barrel 16 that is directly insert molded over the cannula 12. The barrel 16 is preferably comprised of a transparent cyclic olefin copolymer or polymer (COC or COP). The barrel 16 may also be a co-injected or multi-component polymer barrel comprising an alternative enhanced barrier polymer constituent. The distal tip 16a of the barrel 16 extends over a proximal end 12b of the cannula 12 and includes a tapered distal end 17. The cannula 12 is to be securely attached to the distal tip 16a of the barrel 16 that is directly insert molded over the cannula 12. The distal end 17 is generally hollow, so as to form a sleeve around the cannula 12 (FIGS. 1E and 1F). Hollowing out the interior of the distal end 17 around the cannula 12 prevents molten polymeric material from entering into the hollow cannula during the molding process, which would result in an occluded and unusable cannula. Further, hollowing out the interior of the distal end 17 around the cannula 12 reduces the amount of polymeric material in contact with the cannula 12 and therefore further reduces the cooling time required for the insert molding process, as described below. The distal end 17 is sufficiently sized and tapered to allow for cannula or needle shields (not shown), generally manufactured for use with staked glass needles, to be attached to the barrel 16 in a similar manner.

Figure 2A:
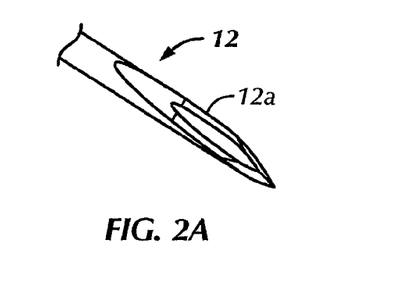
FIG. 2A is a greatly enlarged perspective view of a needle tip of the staked needle shown in FIG. 1A.
Figure 2B:
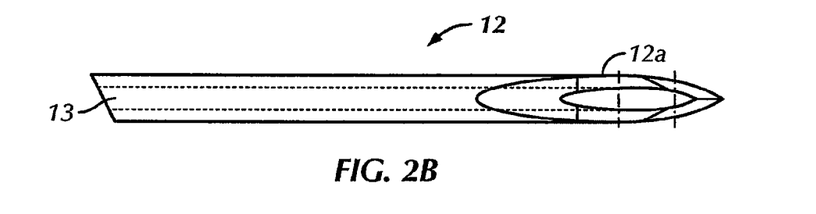
FIG. 2B is a greatly enlarged side elevational view of the needle tip shown in FIG. 2A.
Figure 2C:
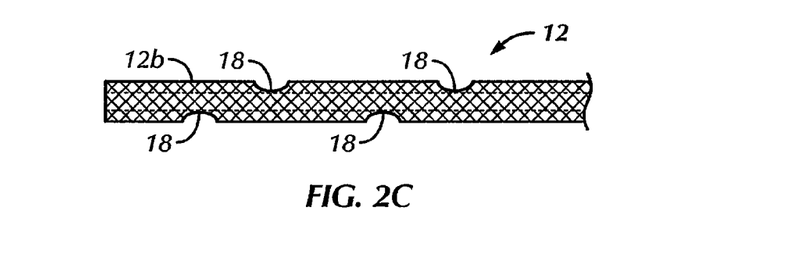
FIG. 2C is a greatly enlarged side elevational view of the proximal end of the needle shown in FIG. 2A.
Figure 3:
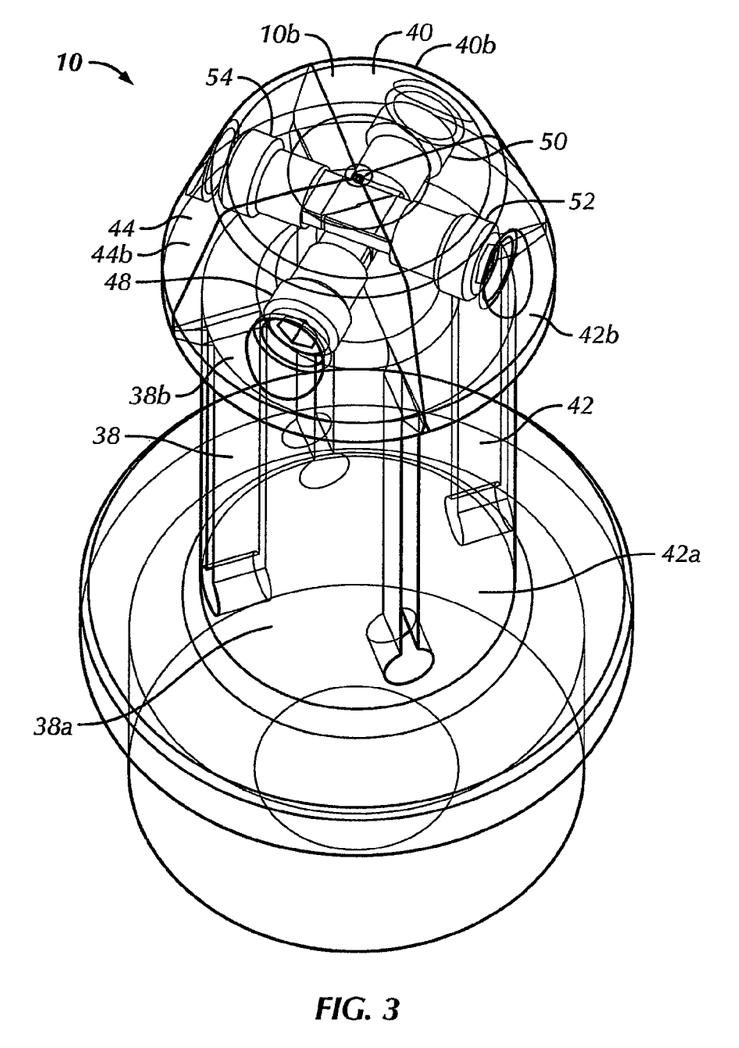
FIG. 3 is a semi-transparent perspective view of a collect mechanism in accordance with the first preferred embodiment of the present invention.
Figure 4:
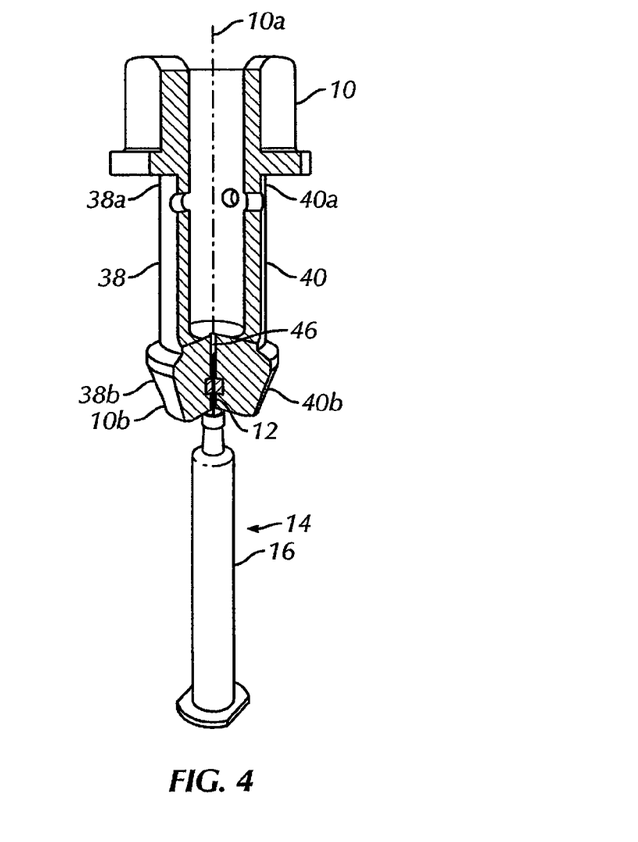
FIG. 4 is a perspective view of a partial collect mechanism shown in FIG. 3 following injection molding with the mold removed.

Referring specifically to FIGS. 2A-2C, the cannula 12 is preferably a fine gauge (i.e. 27 to 33 gauge) hollow metallic needle. A 27 gauge needle typically has a nominal outer diameter of 0.0160 to 0.0165 inch and a nominal inner diameter of 0.0075 to 0.0090 inch. A 33 gauge needle typically has a nominal outer diameter of 0.0080 to 0.0085 inch and a nominal inner diameter of 0.0035 to 0.0050 inch. The interior lumen 13 of the cannula 12 is preferably straight. The cannula 12 preferably has a tip 12a with a three-bevel grind, meaning that the tip 12a is tapered at three distinct angles to reduce the pain perceived by a patient during use of the staked needle 14.

Figures 1A, 1B, 1C, 1D:
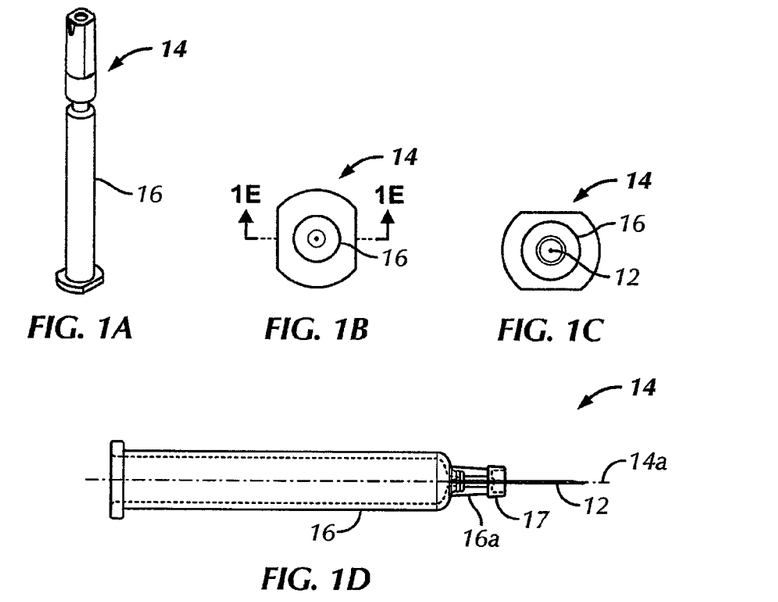
FIG. 1A is a perspective view of a staked needle formed through the use of a collet mechanism in accordance with a first preferred embodiment of the present invention.
FIG. 1B is an enlarged rear elevational view of the staked needle shown in FIG. 1A.
FIG. 1C is an enlarged front elevational view of the staked needle shown in FIG. 1A.
FIG. 1D is an enlarged side elevational view of the staked needle shown in FIG. 1A.
Figure 1E:
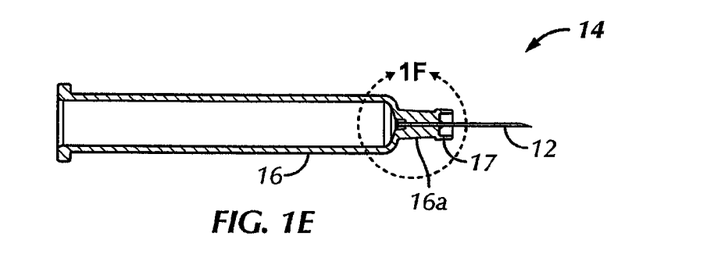
FIG. 1E is an enlarged cross-sectional view of the staked needle shown in FIG. 1A taken along line E-E in FIG. 1B.
Figure 1F:
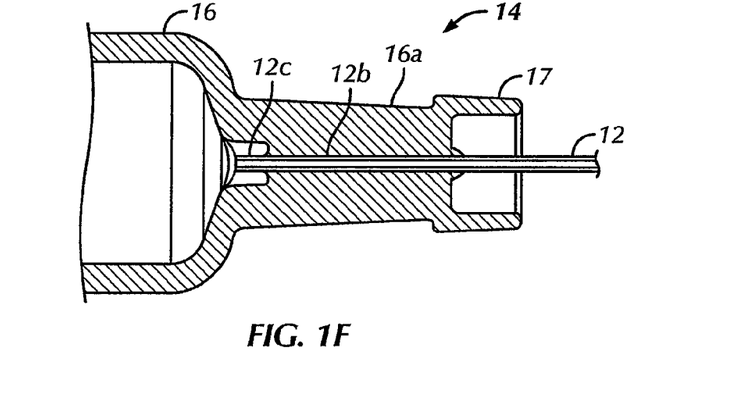
FIG. 1F is a greatly enlarged cross-sectional view of the needle end of the staked needle shown in FIG. 1A taken about area F-F in FIG. 1E.

A plurality of notches 18 are preferably formed on the outer surface of at least a portion of the proximal end 12b of the cannula 12. The notches 18 preferably extend radially inwardly and are axially spaced apart from each other. The notches 18 are preferably machined into the proximal end 12b of the cannula 12. The notches 18 aid in affixing or securing the proximal end 12b of the cannula 12 to the tip 16a of the barrel 16 because the polymeric material forming the tip 16a flows into and fills in the notches 18 during the molding process, as described below, to provide enhanced friction and gripping force between the proximal end 12b and the barrel tip 16a. Because the cannula 12 may not be crimped without potentially damaging the cannula 12 due to its size, the notches 18 which are formed in the cannula 12 replace the function of crimping the cannula 12, as used in the prior art described above. As shown in FIG. 1F, a portion 12c of the proximal end 12b of the cannula 12 extends through the tip 16a and into the barrel 16 due to the molding process, as described further below. At least a portion of the proximal end 12b of the cannula 12 may also be textured or roughened (shown in FIG. 2C with cross hatching) by a mechanical or chemical surface treatment, including ablation, to further enhance the gripping force of the proximal end 12b of the cannula 12 and to better secure the proximal end 12b to the tip 16a of the barrel 16. Though the above described cannula 12 is preferred, it is within the spirit and scope of the present invention that any size and shaped cannula may be used.

Referring to specifically to FIGS. 3-5B, the collet mechanism 10 has first and second axially extending flexible arms 38, 40 that form an expandable internal cavity 46 (see FIGS. 6 and 12), but may include any number of flexible arms. While flexible arms are used in the present embodiment, it would be apparent to one of ordinary skill in the art that any other suitable type of arms may be employed. Preferably, the collet mechanism 10 further includes third and fourth flexible arms 42, 44. Each flexible arm 38, 40, 42, 44 has an attached proximal end 38a, 40a, 42a (the proximal end of the fourth flexible arm 44 obstructed from view) and a free or unattached distal end 38b, 40b, 42b, 44b. The flexible arms 38, 40, 42, 44 may be moved or flexed inwardly and outwardly with the greatest deflection occurring toward the distal ends 38b, 40b, 42b, 44b. The flexible arms 38, 40, 42, 44 are in a closed position (FIGS. 3 and 7) when the distal ends 38b, 40b, 42b, 44b are moved or flexed inwardly, toward the internal cavity 46. The flexible arms 38, 40, 42, 44 are in an open position (FIG. 6) when the distal ends 38b, 40b, 42b, 44b of the flexible arms 38, 40, 42, 44 are moved or positioned away from the internal cavity 46 (e.g., flexed outwardly). The open position of the collet mechanism 10 is preferably the unrestrained state, meaning that the distal ends 38b, 40b, 42b, 44b are untouched, and the closed position of the collet mechanism 10 is preferably the restrained position, meaning that the distal ends 38b, 40b, 42b, 44b are forced together by an outside force, though the opposite configuration may be used if desired.

Figure 5A:
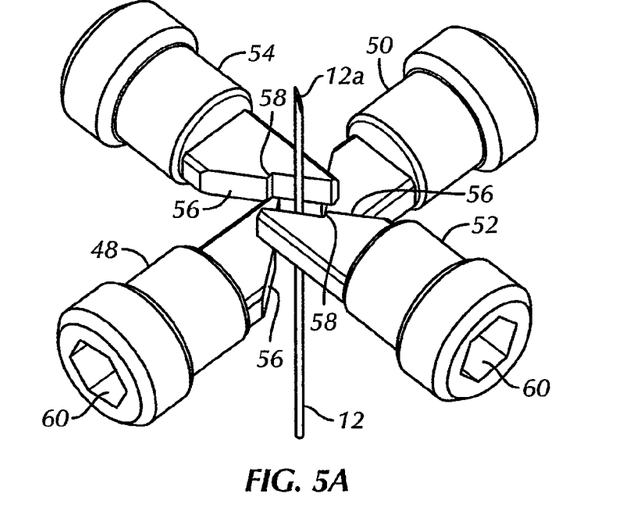
FIG. 5A is an enlarged perspective view of cannula guides of the collet mechanism shown in FIG. 3 in an open position.
Figure 5B:
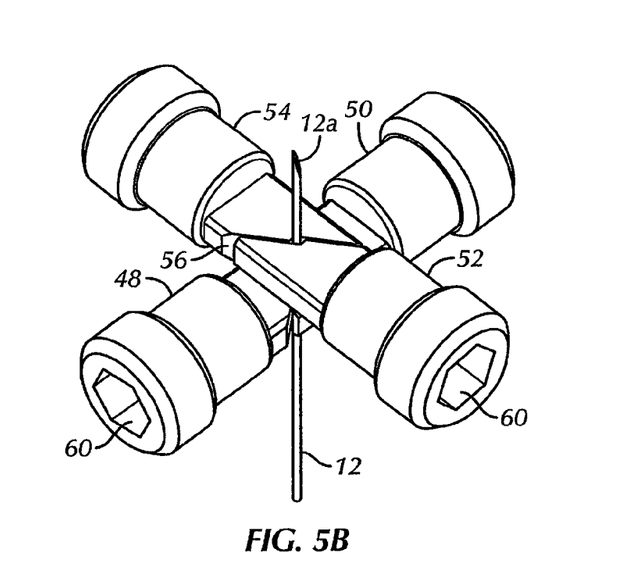
FIG. 5B is an enlarged perspective view of the cannula guides shown in FIG. 5A in a closed position.
Figure 6:
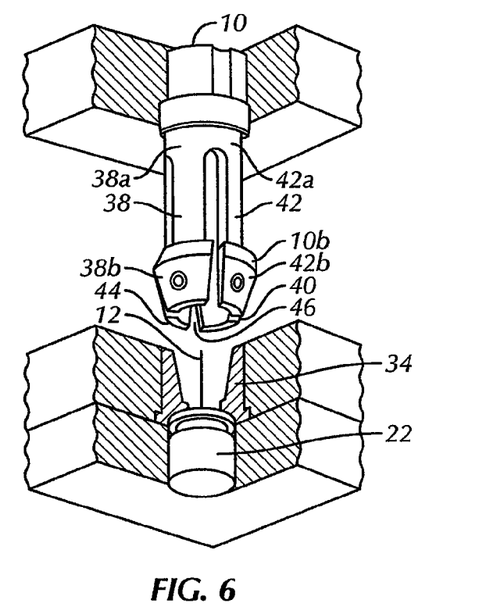
FIG. 6 a perspective schematic view, partially in section, of the collect mechanism and a portion of the mold in an open position.
Figure 7:
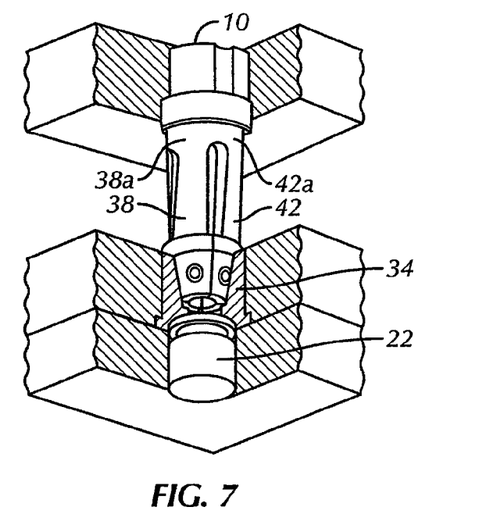
FIG. 7 is a perspective schematic view, partially in section of the collect mechanism and a portion of the mold shown in FIG. 6 in a closed position.

Referring specifically to FIGS. 5A and 5B, the first and second flexible arms 38, 40 include first and second cannula guides 48, 50, respectively. The first cannula guide 48 is preferably directly opposed from the second cannula guide 50. Preferably, the third and fourth flexible arms 42, 44 include third and fourth cannula guides 52, 54, respectively, the third cannula guide 52 preferably being directly opposed from the fourth cannula guide 54. The cannula guides 48, 50, 52, 54 are preferably comprised of a polytetrafluoroethylene material, a plastic with nonstick properties such as TEFLON®, that is gentle on the cannula 12 so as not to indent or alter the outer surface of the cannula 12 when the cannula guides 48, 50, 52, 54 are in contact with the cannula 12, but that resists the elevated temperature of the mold 20. However, the cannula guides 48, 50, 52, 54 may be comprised of any heat resistant polymeric material or some other material, such as stainless steel.

The cannula guides 48, 50, 52, 54 are mounted proximate to and positioned through the distal ends 38b, 40b, 42b, 44b of the respective flexible arms 38, 40, 42, 44 and extend radially at least partially into the expandable internal cavity 46. The cannula guides 48, 50, 52, 54 are preferably generally orthogonal to the flexible arms 38, 40, 42, 44. The cannula guides 48, 50, 52, 54 clamp a portion of the cannula 12 to hold the cannula 12 in place when the flexible arms 38, 40, 42, 44 are in the closed position (FIG. 5B). The cannula guides 48, 50, 52, 54 are spaced away from the cannula 12 when the flexible arms 38, 40, 42, 44 are in the open position (FIG. 5A).

A position of the cannula guides 48, 50, 52, 54 is preferably adjustable with respect to the flexible arms 38, 40, 42, 44 and the internal cavity 46 with a tool, such as an Allen wrench, by inserting the tool into adjustment openings 60 of the cannula guides 48, 50, 52, 54 to position the cannula guides 48, 50, 52, 54 at a predetermined depth into the internal cavity 46. Because the size of the cannula 12 may change and the size of the collet mechanism 10 may vary slightly, the adjustability of the position of the cannula guides 48, 50, 52, 54 allows a user to adjust and set the pressure exerted on the cannula 12 and the resulting force with which the cannula guides 48, 50, 52, 54 contact the cannula 12. Preferably, the position of the cannula guides 48, 50, 52, 54 may be adjusted in accordance with a predetermined force. Thus, the cannula guides 48, 50, 52, 54 can sufficiently position and hold the cannula 12 in the desired position without damaging (i.e. bending, crimping or scratching) the cannula 12, but with sufficient force to retain the cannula 12 without allowing movement during the injection, insert or other molding process. Preferably, the cannula guides 48, 50, 52, 54 exert a predetermined amount of force upon the cannula 12 when in the closed position and in contact with the cannula 12, such that the cannula 12 is not damaged and the sharpness of the tip 12a of the cannula 12 is not altered during the molding process. However, it is within the spirit and scope of the present invention that the cannula guides 48, 50, 52, 54 be immovably mounted to the respective flexible arm 38, 40, 42, 44.

Referring again to FIGS. 5A and 5B, each cannula guide 48, 50, 52, 54 preferably has a sloped mating surface 56 with an indentation or step 58 formed in the center, but may have any mating configuration, such as mating V-shaped members. As shown in FIG. 5B, as the flexible arms 38, 40, 42, 44 move into the closed position, the first and second cannula guides 48, 50 come into mating contact with each other and the third and fourth cannula guides 52, 54 come into mating contact with each other, and all of the cannula guides 48, 50, 52, 54 come into contact with the cannula 12, such that the cannula 12 slides along the sloped mating surface 56 into the indentation 58 of each of the cannula guides 48, 50, 52, 54. When the flexible arms 38, 40, 42, 44 are in the closed position, each indentation 58 abuts the cannula 12, such that the cannula 12 is positioned and held firmly along the center of the collet mechanism 10, generally in alignment with a central longitudinal axis 10a of the collet mechanism 10 (see FIG. 4), and inline with the centerline 14a of the staked needle 14. The cannula guides 48, 50, 52, 54 may mate together in any manner, such as all four guides mating together, as long as the cannula 12 is sufficiently held in place without damage during the injection, insert or other molding process.

Figure 8:
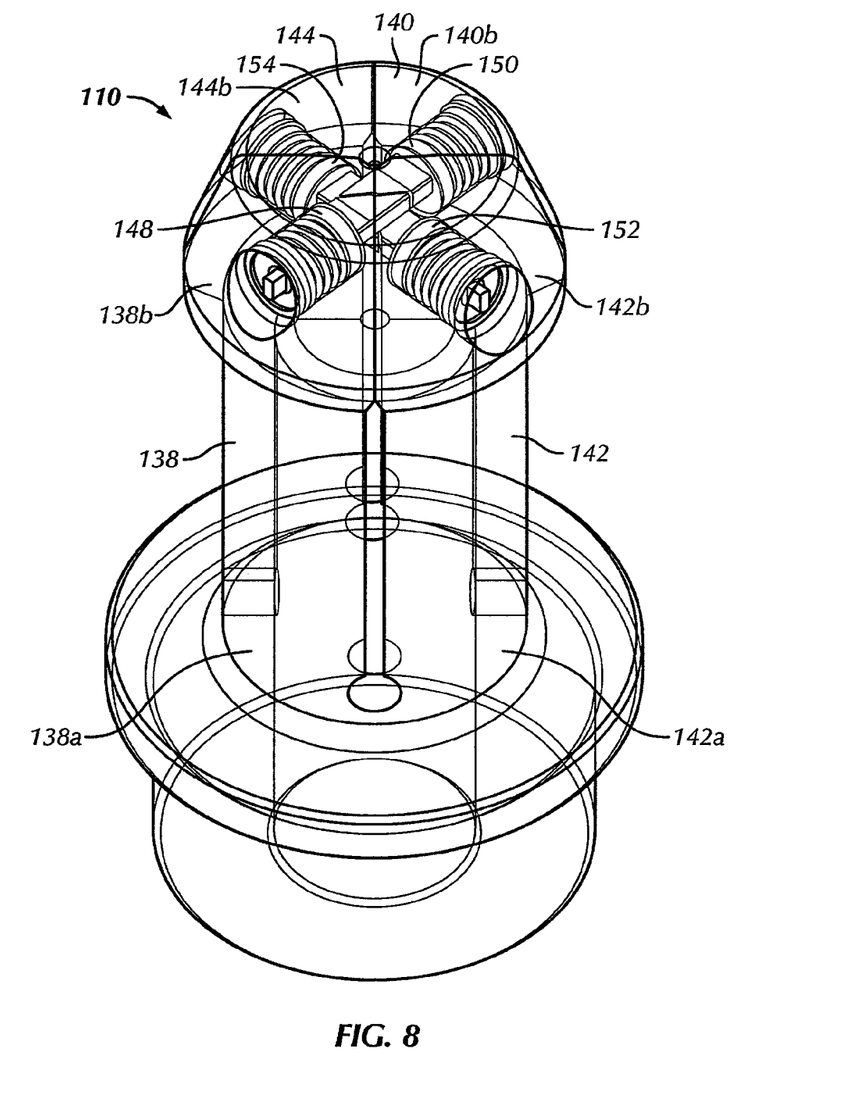
FIG. 8 is a semi-transparent perspective view of a collect mechanism in accordance with a second preferred embodiment of the present invention.
Figure 9:
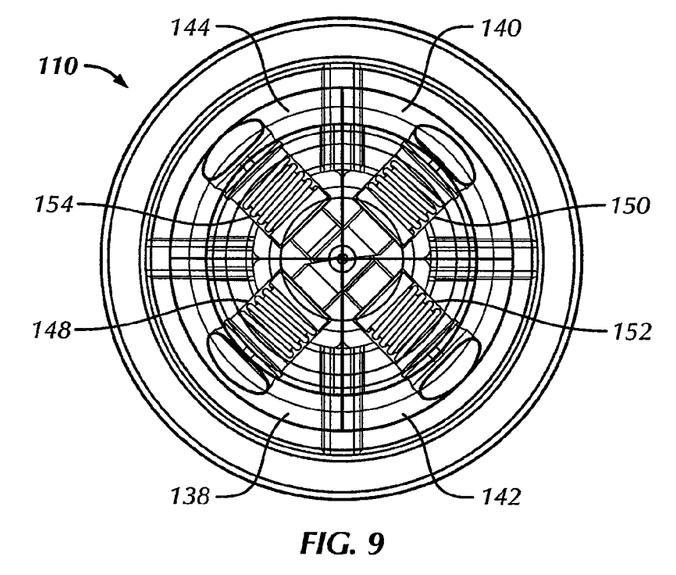
FIG. 9 is a top plan view of the collect mechanism shown in FIG. 8.
Figure 10:
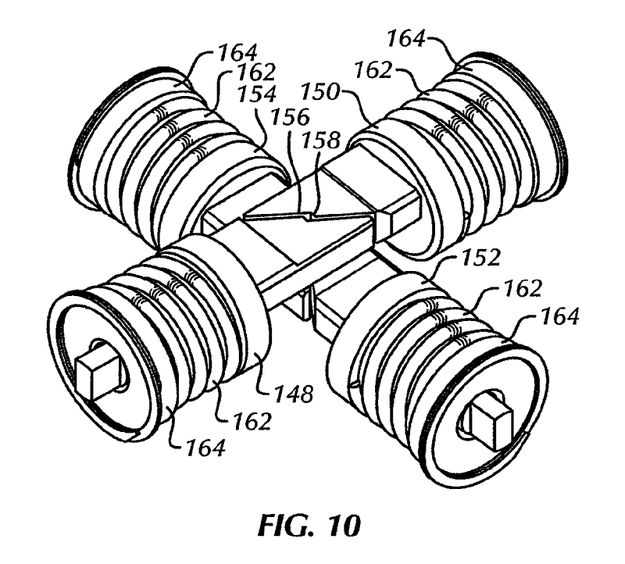
FIG. 10 is a perspective view of cannula guides of the collect mechanism shown in FIG. 8 in a closed position.

Referring to FIGS. 8-10, a second preferred embodiment of the collet mechanism 110 is shown. The collet mechanism 110 is similar to the first preferred embodiment of the collet mechanism 10, except that the cannula guides 148, 150, 152, 154 are each biased toward the closed position. Preferably, each cannula guide 148, 150, 152, 154 includes a coil spring 162 or other suitable biasing member to bias the cannula guides 148, 150, 152, 154. While springs 162 are used to bias the cannula guides 148, 150, 152, 154 in the present embodiment, it would be apparent to one of ordinary skill in the art that any other suitable type of mechanism may be employed. The collect mechanism 110 includes similar elements to the collect mechanism 10 and such elements have been similarly numbered with the addition of a leading one. A mounting member 164 is secured to the distal ends 138b, 140b, 142b, 144b of each of the flexible arms 138, 140, 142, 144. The coil springs 162 are positioned between the mounting members 164 and the cannula guides 148, 150, 152, 154 such that the cannula guides 148, 150, 152, 154 may accommodate differently sized cannulas 12 or may be used in order to ensure that the cannula guides 148, 150, 152, 154 contact and firmly hold the cannula 12 without the need for adjustment. The springs 162 are preferably replaceable such that springs 162 having the desired bias or pressure for the particular cannula size are used. It is within the spirit and scope of the present invention that the first and second embodiments of the collet mechanism 10, 110 be combined such that the cannula guides 48, 50, 52, 54 and 148, 150, 152, 154 may be both adjustable and spring biased.

Figure 11:
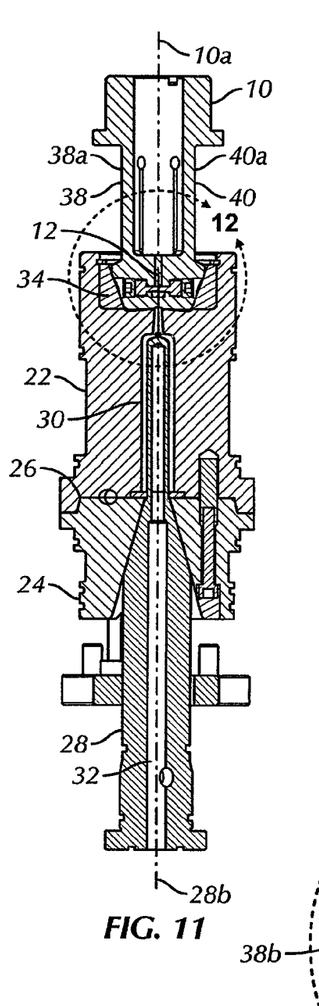
FIG. 11 is a cross sectional view of the collect mechanism shown in FIG. 3 and mold components.
Figure 12:
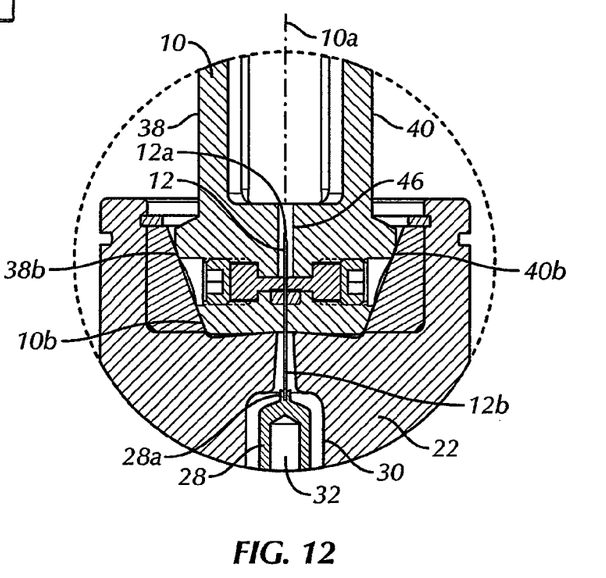
FIG. 12 is a greatly enlarged cross sectional view of the collect mechanism and mold shown in FIG. 11 taken about area 12 in FIG. 11.
Figure 13:
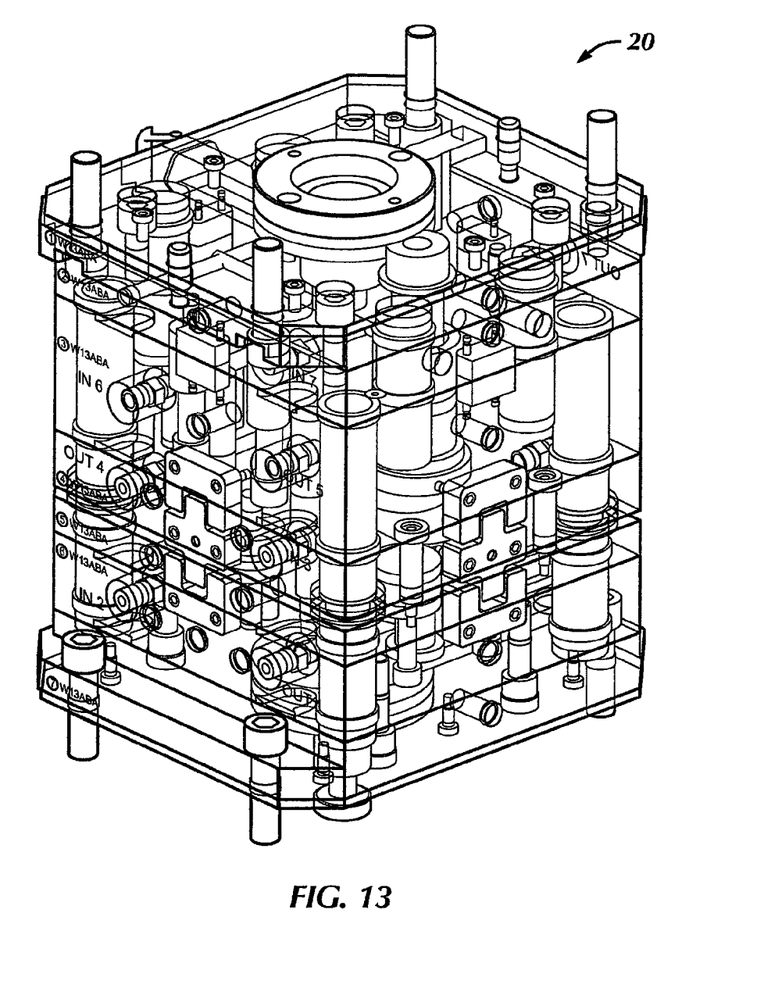
FIG. 13 is a semi-transparent perspective view of the mold encasement for the collet and mold components shown in FIG. 11.

Referring to FIGS. 11-13, the staked needle 14 is manufactured in an insert mold 20 (FIG. 11). The insert mold 20 includes an A-side mold 22 and a B-side mold 24, separable along a parting line 26, shown in FIG. 11. A core member 28, preferably comprised of steel, extends from the B-side mold 24 upwardly and into a mold cavity 30 in the A-side mold 22. The mold cavity 30 is in the shape of the to-be-formed barrel 16. A cooling cavity 32 preferably extends through the center of the core member 28 to cool the core member 28 during molding. The A-side mold 22 includes a conically tapered receiving port 34 positioned above the core member 28 where the tip 16a of the barrel 16 is to be formed. The tapered receiving port 34 at least partially surrounds a portion of the cannula 12.

Referring to FIGS. 6-7 and 11-12, during molding of the staked needle 14, a robotic arm (not shown) transports the cannula 12 and places the proximal end 12b of the cannula 12 onto a recessed tip 28a of the core member 28. The tip 28a of the core member 28 receives the portion 12c of the cannula 12 and positions the cannula 12 generally inline with a center line 14a (see FIG. 1F) of the staked needle 14. The A-side mold 22 is inserted over the steel core member 28 such that the A-side mold 22 contacts the B-side mold 24 along the parting line 26. The tip 12a of the cannula 12 extends at least partially through the receiving port 34.

Once the cannula 12 and A-side mold 22 have been positioned on the core member 28, the collet mechanism 10, preferably having flexible arms 38, 40, 42, 44 with distal ends 38b, 40b, 42b, 44b, is inserted through the A-side mold 22 over the beveled tip 12a of the cannula 12, such that the distal end 10b of the collet mechanism 10 is guided by the tapered receiving port 34 to move the collet mechanism 10 into the closed position. More specifically, the distal ends 38b, 40b, 42b, 44b of the flexible arms 38, 40, 42, 44 are inserted into the tapered receiving port 34 which moves or flexes the flexible arms 38, 40, 42, 44 toward the internal cavity 46 as the distal ends 38b, 40b, 42b, 44b slide along the taper of the tapered receiving port 34, until the collet mechanism 10 abuts the A-side mold 22. Once the collet mechanism 10 abuts the A-side mold 22, or is otherwise stopped, and the distal ends 38b, 40b, 42b, 44b are fully received in the receiving port 34 as shown in FIGS. 11 and 12, the collet mechanism 10 is in the closed position. In the closed position, the cannula guides 48, 50, 52, 54 clamp a portion of the cannula 12 spaced away from the tip 12a of the cannula 12 to hold the cannula 12 generally in alignment with the central longitudinal axis 10a of the collet mechanism 10 and with a central longitudinal axis 28b of the core member 28. The cannula 12 extends beyond the distal ends 38b, 40b, 42b, 44b of the flexible arms 38, 40, 42, 44 and, thus, the collet mechanism 10 does not damage the beveled tip 12a of the cannula 12. Further, in the closed position, the cannula 12 is positioned and firmly held in the center of the internal cavity 46 and is generally inline with the centerline 14a of the staked needle 14 (see FIG. 1D).

Referring specifically to FIG. 11, once the collet mechanism 10 is in place within the A-side mold 22 of the mold 20, molten polymeric material (not shown) is injected into the mold cavity 30 proximate the parting line 26 (dispensing line not shown) until the mold cavity 30 is completely filled with the molten polymeric material. The mold 20 operates at a temperature of approximately 230° F. The mold 20 remains closed and the molten polymeric material is then allowed to cool to a substantially solidified state over at least the proximal end 12b of the cannula 12. It may take approximately 30 seconds for the polymeric material to substantially solidify. Once the polymeric material is cooled to a semi-hardened object, and preferably, a fully hardened object, the collet mechanism 10 and the A-side mold 22 is removed, such that the cannula guides 48, 50, 52, 54 release the cannula 12. The staked needle 14 and attached cannula 12 are then removed from the steel core member 28 by a robotic arm (not shown), and the polymeric material is allowed to further cool and solidify, if necessary, to a fully hardened object.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

Further, to the extent that the method does not rely on the particular order of steps set forth herein, the particular order of the steps in the steps set forth in the preferred method should not be construed as a limitation. One skilled in the art can readily appreciate that the steps may be varied and still remain within the spirit and scope of the present invention.

We claim:

1. A method of manufacturing a syringe comprising the steps of:
    positioning a proximal end of a cannula having an opposing beveled tip onto a recessed tip of a mold core member having an external surface;
    forming a mold cavity space having the shape of a syringe barrel by positioning a mold over the core member and positioned cannula so that at least the proximal end of the positioned cannula is exposed to the mold cavity space and so that the cannula extends through the mold into a tapered receiving port thereof at least partially surrounding the beveled tip of the cannula;
    inserting a collet mechanism having at least two cannula guides in an open position through the mold so that at least a portion of the collet mechanism is positioned within the tapered receiving port of the mold and over the beveled tip of the cannula;
    guiding the collet mechanism against the tapered receiving port into a closed position so that the cannula guides clamp a portion of the cannula to hold the cannula generally in alignment with a longitudinal axis of the collet mechanism and with a longitudinal axis of the core member;
    injecting polymeric material into the mold cavity space and over at least the proximal end of the cannula while the collet mechanism remains closed;
    allowing the polymeric material to cool until substantially solidified over and attached to at least the proximal end of the cannula, thus forming the syringe;
    removing the collet mechanism from the mold so that the cannula guides release the cannula;
    removing the mold; and
    removing the syringe from the core member.

2. The method of claim 1, wherein the cannula guides are positioned opposite each other.

3. The method of claim 1, wherein the collet mechanism comprises four cannula guides.

4. The method of claim 1, wherein a position of each of the cannula guides is adjustable with respect to the collet mechanism and an internal cavity of the collet mechanism so that the force with which the cannula guides clamp the portion of the cannula is adjustable.

5. The method of claim 1, wherein the cannula guides clamp the portion of the cannula at a position spaced away from the beveled tip of the cannula with a predetermined force so that the cannula is not damaged and the sharpness of the beveled tip of the cannula is not altered when the collet mechanism is in the closed position.

6. The method of claim 1, wherein a surface of each of the cannula guides is sloped, the sloped surfaces each having an indentation formed therein.

7. The method of claim 6, wherein the indentations abut the cannula when the collet mechanism is in the closed position.

8. The method of claim 1, wherein at least a portion of the closed collet mechanism forms at least a portion of the periphery of the mold cavity space.

* * * * *